(12) United States Patent
Bormann et al.

(10) Patent No.: US 6,336,916 B1
(45) Date of Patent: Jan. 8, 2002

(54) PRIMING SYSTEM (75) Inventors: Thomas J. Bormann, Melville; Vlado I. Matkovich, Glen Cove; Gerard R. Delgiacco, Yonkers, all of NY (US)

(73) Assignee: Pall Corporation, East Hills, NY (US)

( * ) Notice: Subject to any disclaimer, the term of this patent is extended or adjusted under 35 U.S.C. 154(b) by 0 days.

(21) Appl. No.: 09/171,994

(22) PCT Filed: Apr. 18, 1997

(86) PCT No.: PCT/US97/07706

§ 371 Date: Oct. 29, 1998

§ 102(e) Date: Oct. 29, 1998

(87) PCT Pub. No.: WO97/40870

PCT Pub. Date: Nov. 6, 1997

Related U.S. Application Data (60) Provisional application No. 60/030,490, filed on Nov. 15, 1996, and provisional application No. 60/016,611, filed on May 1, 1996.

(51) Int. Cl.⁷ .................................................. A61M 5/00
(52) U.S. Cl. ........................ 604/251; 604/407; 604/126
(58) Field of Search .................................. 604/251, 252, 604/45, 122, 126, 245–246, 255, 407

(56) References Cited

U.S. PATENT DOCUMENTS

| 1,844,342 A | 2/1932 | Berman |
| 3,042,038 A | 4/1962 | Beacham |
| 3,533,400 A | 10/1970 | Palich |
| 4,116,646 A | * 9/1978 | Edwards |
| 4,136,693 A | 1/1979 | Dyke |
| 4,269,222 A | 5/1981 | Palti |
| 4,340,479 A | 7/1982 | Pall ............................. 210/490 |
| 4,372,306 A | 2/1983 | Genese et al. |
| 4,512,771 A | * 4/1985 | Norton ........................ 604/824 |
| 4,650,458 A | * 3/1987 | Dahlberg et al. ............... 604/5 |
| 4,880,548 A | 11/1989 | Pall et al. .................... 210/767 |
| 4,925,572 A | 5/1990 | Pall ............................. 210/767 |
| 5,069,671 A | 12/1991 | Theeuwes |
| 5,126,054 A | * 6/1992 | Matkovich ................... 210/641 |
| 5,217,627 A | 6/1993 | Pall et al. .................... 210/767 |
| 5,269,917 A | * 12/1993 | Stankowski ................. 210/232 |
| 5,364,526 A | * 11/1994 | Matkovich et al. ......... 210/206 |
| 5,451,321 A | 9/1995 | Matkovich |
| 5,545,339 A | 8/1996 | Bormann et al. |
| 5,779,674 A | * 7/1998 | Ford ............................ 604/126 |
| 5,863,436 A | 1/1999 | Matkovich ................... 210/645 |
| 5,902,281 A | 5/1999 | Kraus et al. |

FOREIGN PATENT DOCUMENTS

| EP | 0062913 | 4/1982 |
| EP | 0165519 | 5/1985 |
| EP | 0787503 | 2/1997 |
| FR | 2390174 | 5/1978 |
| WO | WO91/17809 | 11/1991 |

* cited by examiner

*Primary Examiner*—Sharon Kennedy
*Assistant Examiner*—Catherine Serke
(74) *Attorney, Agent, or Firm*—Leydig, Voit, & Mayer, Ltd.

(57) ABSTRACT

A device (100) such as a drip chamber that can be filled to a predetermined level is disclosed. The device comprises a housing (14) and a porous medium (10), wherein the porous medium allows gas to pass therethrough.

29 Claims, 7 Drawing Sheets

PRIMING SYSTEM

This application claims the benefit of U.S. provisional patent applications 60/016,611, filed May 1, 1996, and 60/030,490, filed Nov. 15, 1996, which are incorporated by reference in their entireties.

TECHNICAL FIELD

This invention relates to a device and method for transferring fluid, especially for venting and/or priming fluid transfer and/or processing systems. The present invention is particularly useful in the administration of parenteral fluids, e.g., drugs, nutrients, hydration solutions, and/or transfusion products such as blood components.

BACKGROUND OF THE INVENTION

Many fluid transfer systems such as fluid processing systems function more efficiently if they can be at least partially purged of air or gas before use. For example, it may be desirable to prime a fluid transfer system, e.g., to displace or remove air from one or more devices and/or tubes in the system to allow them to be filled with liquid before continuously operating the system. Since pockets of air or gas can block or slow the flow of liquid, minimizing or eliminating the presence of air or gas can allow the liquid to flow more quickly through the system.

Additionally, some transfer systems, e.g., for administering fluid to a patient, should minimize or prevent air or gas from passing beyond a certain location in the system. For example, some intravenous (IV) systems include a drip chamber or a bubble trap to capture air or gas so that it will not be administered to the patient. The drip chamber can also be used to allow the operator of the system to monitor the rate at which the fluid is administered. For example, the operator may observe the drip chamber to ensure that the patient is receiving the liquid at a given rate, e.g., a rate of so many drops of liquid per minute. If desired, the rate can be changed and the new rate can be monitored by observing the rate at which the drops of liquid pass through the chamber.

There are drawbacks to conventional fluid transfer systems. For example, some systems for administering transfusion products require a labor intensive effort by the operator of the system. Illustratively, when transfusing blood or blood products, especially when filtering and administering blood at the patient's bedside, the operator of the system may have to start the flow of blood from the source bag with the drip chamber initially inverted until the drip chamber is about ⅔ full. Then the partially filled drip chamber is placed in the upright position and the system is primed. After the system is primed, blood can be administered, and the rate monitored through the drip chamber.

The operator must carefully monitor the initial filling of the inverted drip chamber, since overfilling the chamber leads to difficulties in monitoring the drip rate. For example, a high level of fluid in the chamber can provide insufficient space for a drop to form before it contacts the fluid in the chamber, making it difficult to count drops. On the other hand, underfilling the chamber increases the possibility that air will pass through the chamber, with possibly adverse consequences for the patient.

Accordingly, there is a need in the art for a device and method that provides for efficient priming of a fluid processing system, e.g., that allows a drip chamber to be filled to a desired level without a labor intensive effort. In particular, there is a need in the art for a "level setting" drip chamber, that automatically vents air or gas, without overfilling.

The present invention provides for ameliorating at least some of the disadvantages of the prior art. These and other advantages of the present invention will be apparent from the description as set forth below.

SUMMARY OF THE INVENTION

In accordance with an embodiment of the present invention, a device for use in a fluid transfer system is provided that vents gas, without overfilling with liquid. Illustratively, gas can be vented from a flow metering device such as a drip chamber, and the drip chamber can be filled to a desired level of liquid, wherein the amount of liquid in the chamber is less than the total liquid capacity of the chamber. In a more preferred embodiment, the device vents gas, and seals after venting, without overfilling with liquid.

In an embodiment, once fluid flow toward the device is initiated by the operator of the fluid transfer system, the device automatically vents gas and fills to a desired level, without operator involvement. For example, the operator does not need to squeeze and/or invert the device. Moreover, the device can be filled with liquid, and subsequently utilized during administration of the liquid, while keeping the device in an essentially upright position, and without allowing gas or air to enter the device through the vent.

SPECIFIC DESCRIPTION OF THE INVENTION

In accordance with the present invention, a device for transferring fluid is provided comprising a housing comprising a fluid reservoir for gas and liquid; a vent communicating with the housing, the vent comprising a liquid sealable porous medium that allows gas in the housing to pass through the medium until the medium is contacted by the liquid, the vent and the housing being cooperatively arranged to allow the gas to be vented from the housing and for liquid to fill the housing to a predetermined level that is less than the total liquid capacity of the housing.

The present invention also provides a device for transferring fluid comprising a housing having a fluid reservoir for gas and liquid; a vent communicating with the housing, the vent comprising a porous medium that allows gas in the housing to pass through the medium until the medium is contacted by the liquid, the vent and the housing being cooperatively arranged to allow the gas to be vented from the housing and for liquid to fill the housing to a predetermined level that is less than the total liquid capacity of the housing.

In some embodiments, the device for transferring fluid comprises a flow metering device such as a drip chamber. The device may also include a structure such as a cap, plug, and/or valve capable of engaging with the housing, e.g., to cover and/or seal the vent.

The present invention also provides a drip chamber comprising a housing including a porous medium that allows liquid to fill the housing to a predetermined level without completely filling the housing with liquid, the medium allowing gas to pass from the housing until the medium is contacted by the liquid, the medium including a liquophilic element and a liquophobic element.

In accordance with the invention, a system for transferring at least one fluid is provided, the system comprising the device for transferring fluid, and a container suitable for holding a fluid to be transferred, wherein the device is in fluid communication with the container. In an embodiment, the device comprises a drip chamber, and the system also includes a filter, e.g., a blood filter such as a leukocyte filter, interposed between the drip chamber and the container. In some embodiments, the system includes a plurality of containers, e.g., suitable for holding different fluids to be transferred.

An embodiment of a system for transferring at least one fluid in accordance with the invention comprises the device for transferring fluid, and a filter suitable for filtering a fluid to be transferred, wherein the device is in fluid communication with the container.

The present invention also provides a method for transferring one or more fluids comprising passing a fluid into a device comprising a housing including a fluid reservoir for gas and liquid, and a vent communicating with the housing, the vent comprising a liquid sealable porous medium that allows gas in the housing to pass through the medium until the medium is contacted by a liquid; passing liquid into the housing and passing gas through the porous medium until the liquid contacts the porous medium and the housing is filled to a predetermined level that is less than the total liquid capacity of the housing.

In accordance with embodiments of the invention, the transferred fluid or fluids are transferred to a desired location, e.g., the fluids are transferred to a container, or are administered to a patient. In an embodiment, one of the fluids to be transferred is a biological fluid such as blood or a blood component, and the method also includes administering the biological fluid to a patient. For example, a first fluid, e.g., a non-biological fluid such as saline, can be passed through the device and administered, and subsequently a second fluid such as a biological fluid can be passed through the device and administered. In some embodiments, the method includes filtering one or more fluids, e.g., to remove undesirable material therefrom, before administering the fluid(s). Illustratively, at least one fluid such as a biological fluid, e.g., blood, a blood product, or a blood component, can be filtered to remove undesirable material such as leukocytes therefrom, before administering the biological fluid to the patient.

Embodiments of the present invention provide for efficient separation of gas or air from a fluid flow path. More preferred embodiments provide for efficient separation of gas or air from fluid delivery systems, e.g., systems involving parenterally administered fluids, such as intravenously administered liquids, for example, biological fluids such as blood, blood products, and blood components; drugs and/or nutrients. Thus, gas can be separated from the fluid delivery system, e.g., vented to the atmosphere, or the gas can be directed to a desired location within the system, e.g., away from a desired liquid flow path. As used herein, the term "gas" includes air.

In accordance with the invention, a biological fluid includes any treated or untreated fluid associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), platelet-rich plasma (PRP), platelet-poor plasma (PPP), platelet-free plasma, plasma, fresh frozen plasma (FFP), components obtained from plasma, packed red cells (PRC), transition zone material or buffy coat (BC); blood products derived from blood or a blood component or derived from bone marrow; red cells separated from plasma and resuspended in a physiological fluid; and platelets separated from plasma and resuspended in a physiological fluid. The biological fluid may have been treated to remove some of the leukocytes before being processed according to the invention. As used herein, blood product or biological fluid refers to the components described above, and to similar blood products or biological fluids obtained by other means and with similar properties.

A "unit" is the quantity of biological fluid from a donor or derived from one unit of whole blood. It may also refer to the quantity drawn during a single donation. Typically, the volume of a unit varies, the amount differing from patient to patient and from donation to donation. Multiple units of some blood components, particularly platelets and buffy coat, may be pooled or combined, typically by combining four or more units.

Each of the components of the invention will now be described in more detail below. Like components have like reference numbers.

Figure 9:
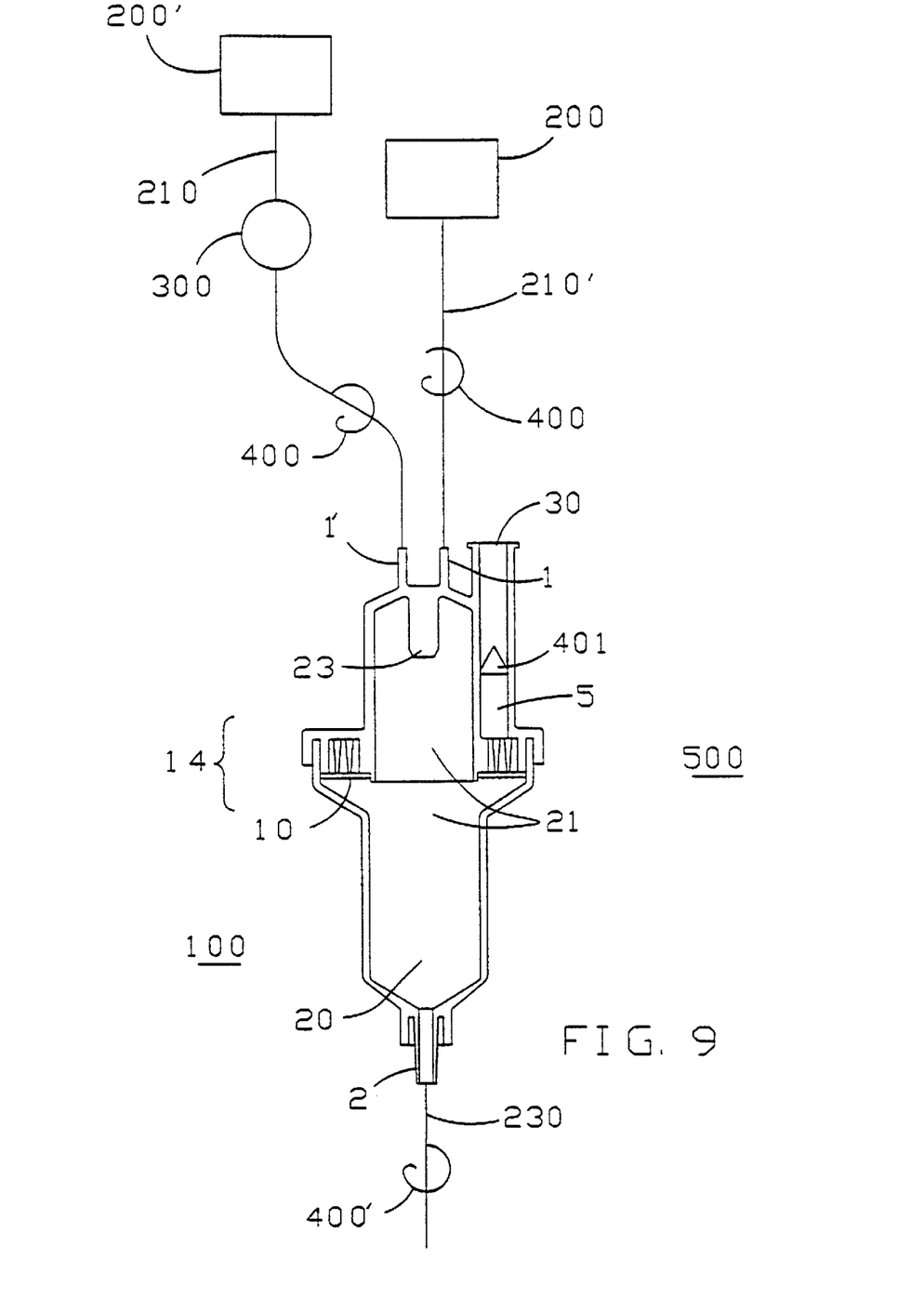
FIG. 9 is an embodiment of another fluid processing system according to the present invention, including a cross-sectional view another embodiment of a venting device.

In the exemplary embodiment illustrated in FIGS. 1–5, and 9, device 100 includes a housing 14, having at least one inlet 1 and an outlet 2; a lumen 21 for fluid flow between the inlet and the outlet; and a vent 3 providing a gas flow path. Vent 3 comprises a porous medium 10 that allows gas, but not liquid, to pass from the lumen 21 through a port 4 into a gas passageway 5 and through a port 30. Typically, porous medium 10 is located in the housing 14, and has a surface 10a facing the inlet 1, and a surface 10b facing the outlet 2. Preferably, porous medium 10 has a portion of the surface 10a near or adjacent to port 4 of gas passageway 5. In some embodiments, e.g., as illustrated in FIG. 9, the device 100 includes at least two inlets 1, 1'.

Figure 1:
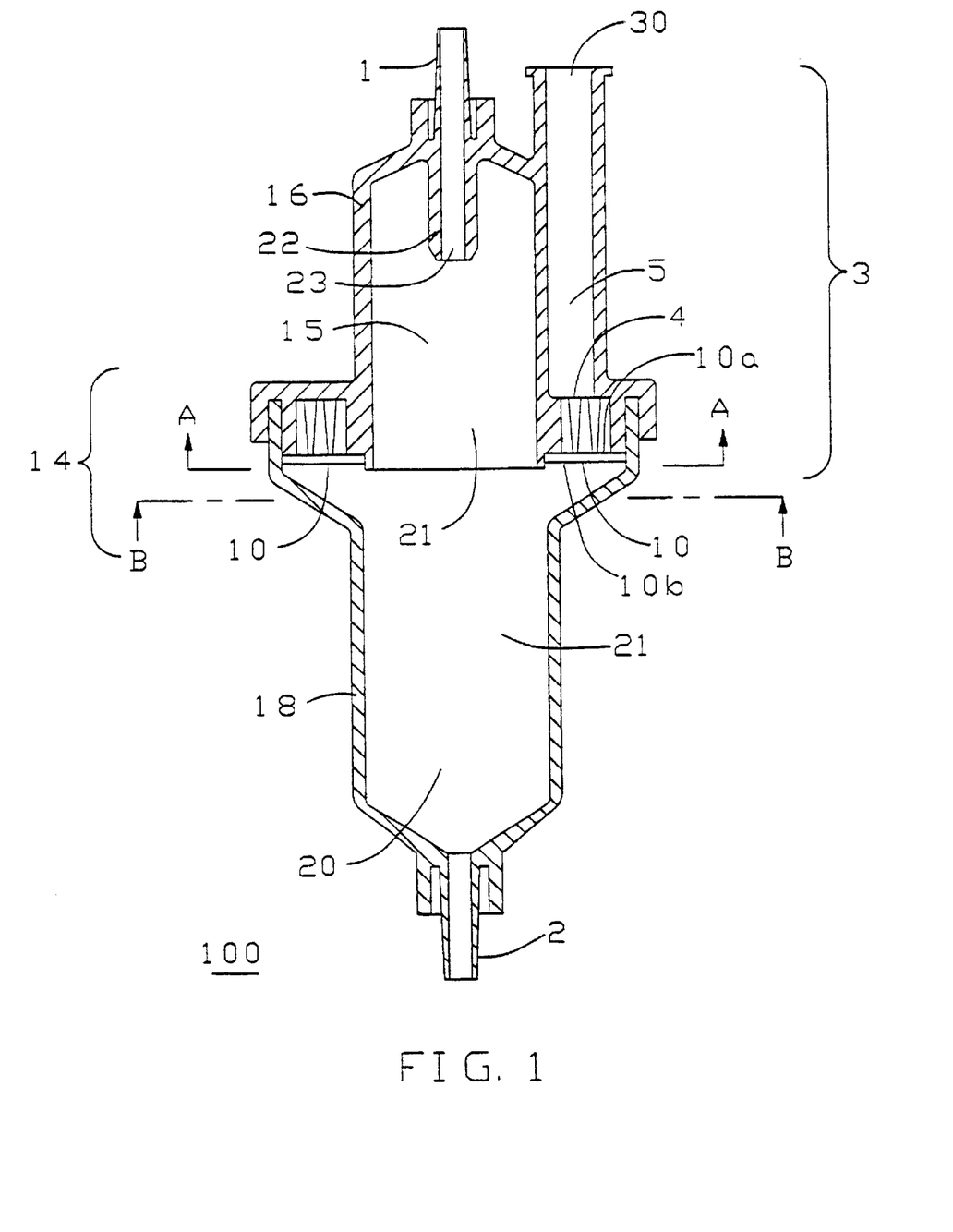
FIG. 1 is a cross-sectional view an embodiment of a venting device according to the present invention.
Figure 3:
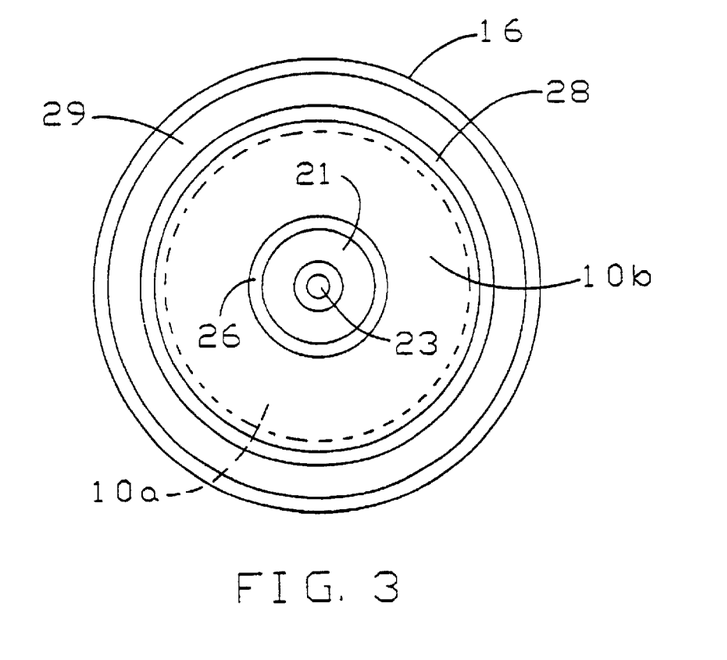
FIG. 3 is a view of the device of FIG. 2 along line B—B, showing a porous medium for passing gas therethrough located in the device.
Figure 4:
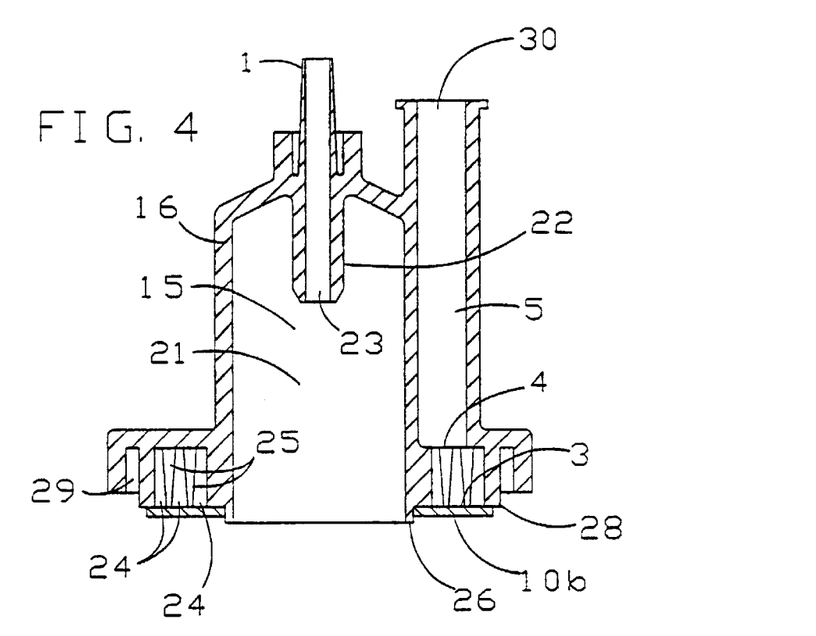
FIG. 4 is a cross-sectional view of the upper chamber and the porous medium of the device of FIG. 1.

Typically, as illustrated in FIGS. 1, 3, and 4, housing 14 includes a first portion 16, having an inlet 1, and a groove 29. The first portion 16 also includes a nipple 22 having a port 23 leading to lumen 21. Preferably, the nipple 22 and port 23 allow liquid to enter the lumen 21 in the form of droplets.

Figure 5:
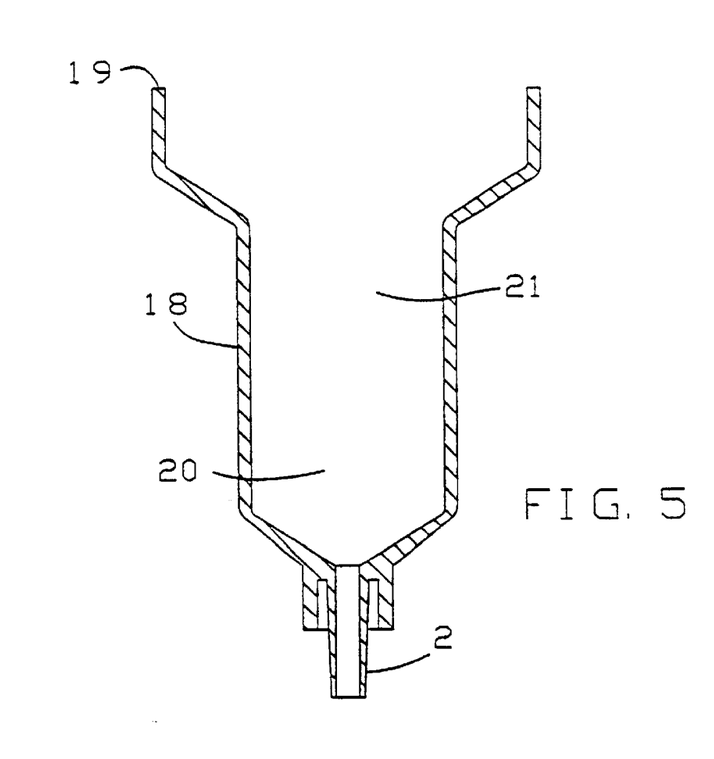
FIG. 5 is a cross-sectional view of the lower chamber of the device of FIG. 1.

As illustrated in FIGS. 1 and 5, housing 14 also includes a second portion 18 having an outlet 2, and a lip 19. In the embodiment shown in FIG. 1, the first portion 16 and the second portion 18 are sealed to form a first chamber 15 and a second chamber 20 encompassing lumen 21 and porous medium 10.

Figure 2:
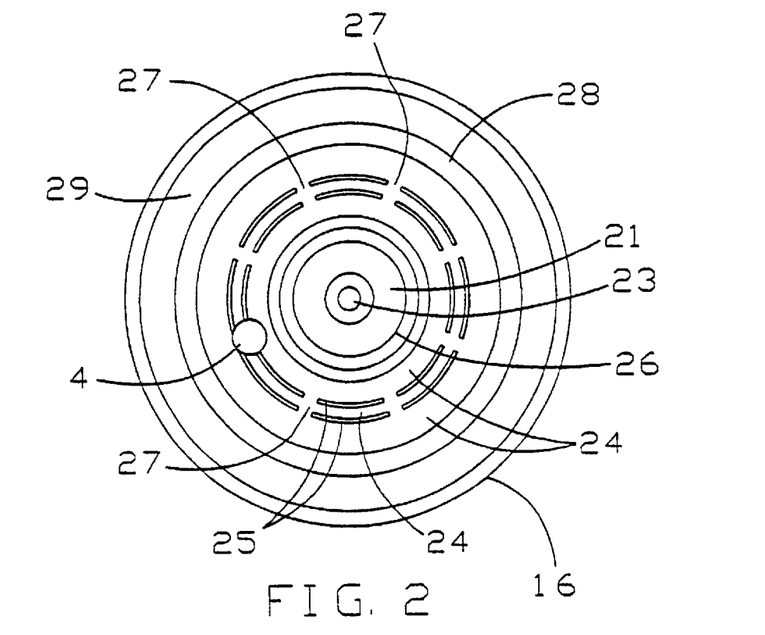
FIG. 2 is a view of the device of FIG. 1 along line A—A.

Preferably, as illustrated in FIGS. 2 and 3, porous medium 10 is annular in shape, and surface 10a faces a series of ribs 25, 26, 28, and/or channels 24, 27 in the first portion 16. Typically, in those embodiments having an annular porous medium 10, the ribs 25, 26, and 28, and the channels 24 are generally concentric. In the illustrated embodiment, first portion 16 also includes radial channels 27.

In an embodiment, the device 100 includes a flow control device 401, e.g., a valve as illustrated in FIG. 9. Exemplary flow control devices 401 comprise check valves or one-way valves.

Figure 8:
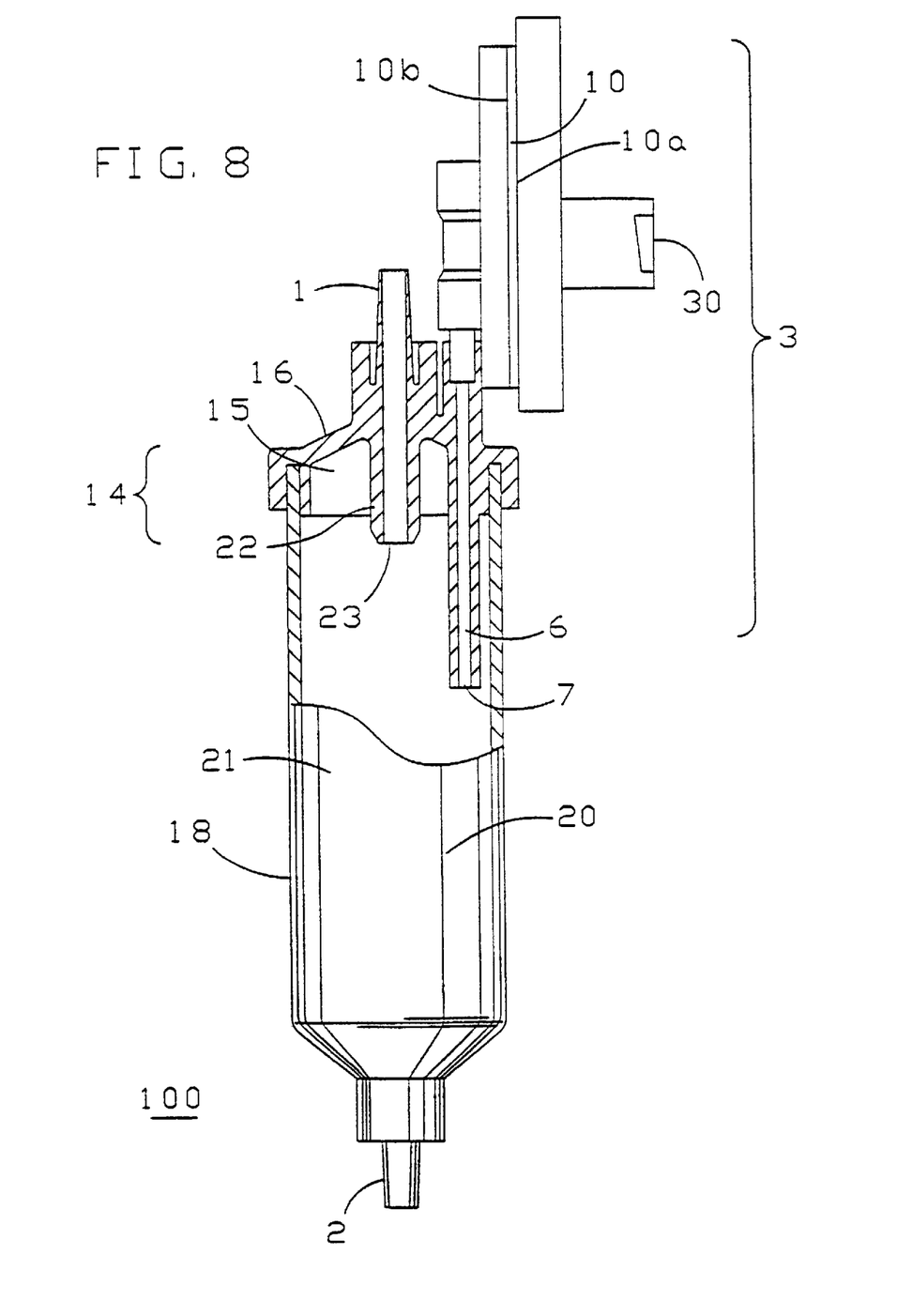
FIG. 8 is a cross-sectional view of another embodiment of a venting device according to the present invention.

In another embodiment as illustrated in FIG. 8, the porous medium 10 is located more exteriorly to housing 14. For example, porous medium 10 can be disposed in a separate vent housing 50 adjacent housing 14. Gas and liquid pass from lumen 21 through port 7 and passageway 6 to porous medium 10 in vent housing 50. Porous medium 10 allows gas, but not liquid, to pass therethrough to port 30.

Figure 6:
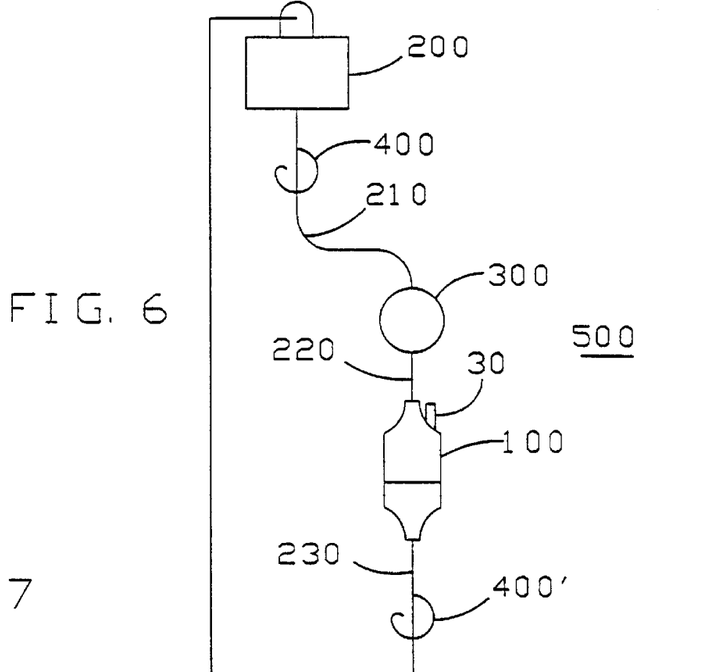
FIG. 6 is an embodiment of a fluid processing system according to the present invention, including a venting device, and a device for filtering biological fluid.
Figure 10:
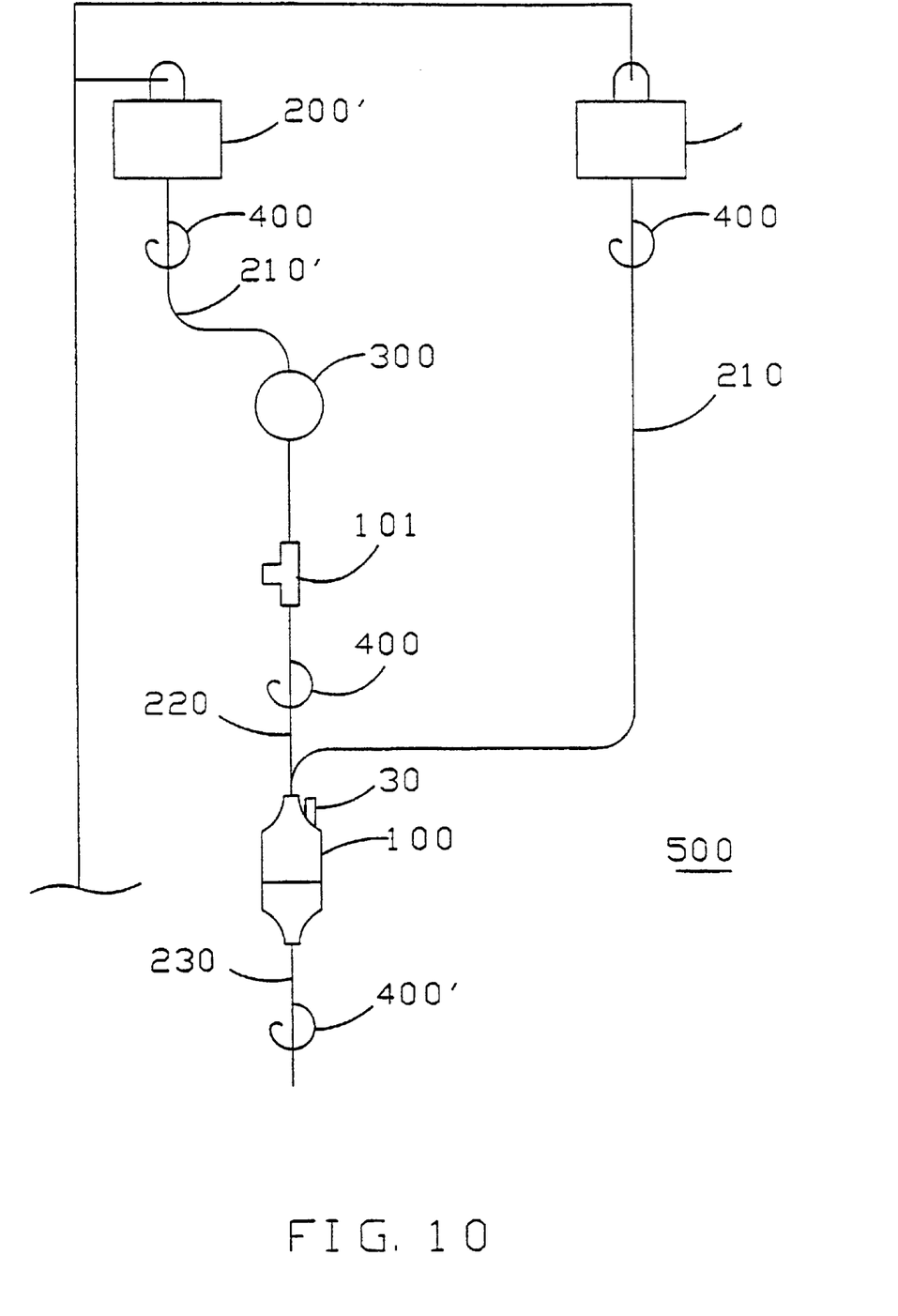
FIG. 10 is an embodiment of another fluid processing system according to the present invention, including a venting device, a device for filtering biological fluid, and a plurality of containers.

FIGS. 6, 7, 9 and 10 illustrate embodiments of a typical system 500 utilizing device 100 during the transfer of at least one fluid to a desired destination. For example, the embodiments of the systems are especially useful for the administration of at least one fluid such as a parenteral fluid to a patient. FIGS. 6, 9, and 10 also include an optional filter 300, e.g., for filtering a fluid before administering it to the patient. The illustrated embodiments of the system include a container 200 for holding a fluid such as a parenteral fluid, wherein the container is in fluid communication, via conduits such as conduits 210, 210', 220 and 230, with the filter 300 (if present), the device 100, and the destination of the fluid, e.g., a patient. In some embodiments, e.g., as illustrated in FIGS. 9 and 10, the system includes two or more containers 200, 200' for holding fluid.

Typically, in those embodiments of a system that include a plurality of containers, the containers hold different parenteral fluids. Illustratively, using the embodiments of the systems illustrated in FIGS. 9 and 10 for reference, container 200' may be suitable for holding one fluid, e.g., a biological fluid such as blood, one or more blood products, or one or more blood components, and container 200 may be suitable for holding another fluid, e.g., a non-biological fluid that is compatible with the biological fluid, such as saline.

The system also includes at least one, and more preferably at least two, flow control devices 400,400' such as clamps. Typically, the system, which can be open or closed, includes one or more connectors. For example, in some embodiments, the system includes a "spike" for connecting a conduit to a container. Of course, in other embodiments, components of the system can be connected in accordance with other protocols known in the art, e.g., via sterile docking.

It is intended that the present invention is not to be limited to the above listed components of the system. For example, the system may have components such as, but not limited to, connectors, additional containers, injection ports, and additional vents such as gas inlets and/or gas outlets. For example, FIG. 10 illustrates an embodiment of a system including an additional vent 101 comprising a gas inlet and/or gas outlet, wherein the vent 101 includes a porous medium suitable for passing gas therethrough.

As noted above, the embodiments of the device and system provide for venting gas, and vent 3 provides a gas flow path, wherein gas, but not liquid, passes through a porous medium 10. Porous medium 10, which is preferably a membrane or film, includes at least a liquophobic portion, and preferably includes a liquophobic portion and a liquophilic portion. Even more preferably, the porous medium 10 includes at least one liquophobic porous element or layer and at least one liquophilic porous element or layer. Typically, a liquophobic element is superimposed on a liquophilic element. Preferably, the liquophobic element or layer is hydrophobic, and the liquophilic element or layer is hydrophilic. In some of the embodiments wherein the porous medium 10 lacks a liquophilic element or layer, the liquophobic element or layer is hydrophobic.

Both the liquophobic and the liquophilic elements or layers allow gas to pass through. However, the liquophobic element is not wettable, or poorly wettable, by the liquid being transferred in the system, and the liquophilic element is wettable by the liquid. Once the liquophilic element is contacted or covered (e.g., wetted) by the liquid being transferred, gas flow through the vent 3 stops, and the medium 10 is sealed. Once the medium is sealed, gas or air external to the device 100 is also prevented from flowing through the medium, even when the level of liquid in the device subsequently decreases. Of course, particularly when the device 100 is left essentially unattended while fluid is being administered, it may be additionally desirable to block or seal the port 30, e.g., with a cap or cover, after gas has been vented and the liquophilic element has been wetted. In those embodiments wherein the porous medium 10 lacks a liquophilic element or layer, after the liquophobic element has been covered by the liquid, the port 30 should be blocked or sealed, at least temporarily, to prevent gas external to the device 100 from entering the device through the port.

In the embodiment shown in FIG. 1, porous medium 10 includes a first surface 10a and a second surface 10b. In some embodiments, porous medium 10 includes two layers, e.g., superimposed layers, with surface 10a representing the surface of liquophobic layer that is not facing the liquophilic layer, and with surface 10b representing the surface of liquophilic layer that is not facing the liquophobic layer. As illustrated in FIGS. 2–4, a portion of surface 10a is near or adjacent port 4 at the end of gas passageway 5. In another embodiment including superimposed layers, as illustrated in FIG. 8, a portion of surface 10b is near or adjacent port 7 at the end of passageway 6.

In accordance with one embodiment according to FIGS. 1–3, the porous medium 10 comprises the liquophobic element and the liquophilic element arranged in the housing 14 to vent gas through gas passageway 5 until the liquophilic element is contacted or covered by the liquid being transferred.

Similarly, in accordance with one embodiment according to FIG. 8, the medium 10 comprises the liquophobic element and the liquophilic element arranged near the housing 14 to vent gas from passageway 6 until the liquophilic element is contacted with, or covered by, the liquid being transferred.

In some of the preferred embodiments, gas flow automatically stops when the liquophilic element is wetted, without liquid substantially passing through the liquophobic element. Once the gas flow stops, the device 100 has been filled to the desired level, without overfilling. Gas remaining in the interior of the housing 14 will not be displaceable, and the liquid will stop rising in the housing. Furthermore, once the liquophilic element is wetted, the medium 10 is sealed, preventing gas from entering the device 100 through the medium.

In those embodiments wherein the porous medium 10 includes a liquophobic element and lacks a liquophilic element, gas flow automatically stops when the liquophobic element is covered with liquid, without the liquid substantially passing through the liquophobic element. Once the gas flow stops, the device 100 has been filled to the desired level, without overfilling. Gas remaining in the interior of the housing 14 will not be displaceable, and the liquid will stop rising in the housing.

A variety of materials may be used, provided the requisite properties of the porous medium 10 are achieved. These properties include the necessary strength to handle the differential pressures encountered in use and the ability to provide the desired permeability without the application of excessive pressure. Suitable starting materials include synthetic polymers including polyamides, polyesters, polyolefins, particularly polypropylene and polymethylpentene, perfluorinated polyolefins, such as polytetrafluoroethylene, polysulfones, polyvinylidene difluoride, polyacrylonitrile and the like, and compatible mixtures of polymers. Within the class of polyamides, suitable polymers include, for example, polyhexamethylene adipamide, poly-ϵ-caprolactam, polymethylene sebacamide, poly-7-aminoheptanoamide, polytetramethylene adipamide (nylon 46), polyhexamethylene azeleamide, and polyhexamethylene adipamide (nylon 66). In an embodiment, skinless, substantially alcohol-insoluble, hydrophilic polyamide membranes, such as those described in U.S. Pat. No. 4,340,479, are suitable.

Typically, the porous medium 10 has a pore size of about 5 micrometers or less, more preferably, about 3 micrometers or less, even more preferably, about 2 micrometers or less. In those embodiments including administering fluid(s) to a patient, the medium 10 typically has a bacterial blocking pore structure to preclude bacteria from entering the system through the vent. For example, the medium can have a pore size of about 0.2 micrometer or less. In those embodiments having liquophobic and liquophilic layers, either or both layers can have the bacterial blocking pore structure.

The device can include additional layers or elements, e.g., for use as spacers and/or supports with respect to the porous medium 10. An exemplary support or spacer layer can be a mesh or screen.

Exemplary porous media 10, including liquophobic and liquophilic elements, include those disclosed in International Publication No. WO 91/17809 and U.S. Pat. Nos. 5,126,054 and 5,451,321.

The housing 14 can be fabricated from any suitable impervious material, preferably a rigid material, such as any thermoplastic material, which is compatible with the fluid being processed. For example, the housing can be fabricated from a metal, or from a polymer. In an embodiment, the housing is a polymer, preferably a transparent or translucent polymer, such as an acrylic, polypropylene, polystyrene, or a polycarbonated resin. Such a housing is easily and economically fabricated, and allows observation of the passage of the liquid through the housing.

The surfaces of the housing contacting the fluid may be treated or untreated. For example, the surfaces of the housing contacting the fluid may be rendered liquophilic for better priming. Methods for treating the surface of the housing include but are not limited to radiation grafting and gas plasma treatment.

The housing may be configured for ease of use. For example, the housing may a include a bracket or hook for ease of mounting or support during administration of a parenteral fluid.

The housing can be sealed as is known in the art. For example, first portion 16 and second portion 18 can be welded together, e.g., after fitting lip 19 into groove 29. Additionally, the porous medium 10 can be sealed within the housing 14 to achieve convenience of use, rapid priming, and efficient gas clearance. Suitable methods for sealing, fitting, and/or bonding the medium within or to the housing are known in the art. For example, the porous medium 10 can be compression sealed or interference fit within the housing, or bonded to the housing. The porous medium can be welded to the housing, e.g., heat welded or ultrasonically welded.

The housing 14 can include an arrangement of ribs, walls or projections, or may comprise one or more channels, grooves, conduits, passages, or the like which may be serpentine, parallel, curved, radial, spiral, or have a variety of other configurations. Typically, at least one projection faces the first surface 10a and/or faces the second surface 10b of the porous medium 10. The ribs, walls or projections may be used to define the channels, grooves, conduits, or passages. Typically, the housing 14 includes at least one rib, wall, or projection to support and/or position the porous medium 10 within the housing. In some embodiments, the housing includes at least one rib, wall or projection to improve the efficiency of gas flow, e.g., by supporting or positioning the porous medium 10 within the housing while providing clearance between portions of the first surface 10a and the housing.

Typically, as illustrated in FIG. 2 first portion 16 includes ribs 25 and channels 24, which are preferably concentric ribs and channels, to allow more efficient flow of gas to the gas passageway 5. The first portion can also have radial channels 27, and at least one, more preferably, at least two, additional ribs such as concentric ribs 26 and 28. FIGS. 2 and 3 also illustrate rib 26, that preferably positions the medium 10 with respect to first portion 16.

In the embodiment illustrated in FIG. 1, the first portion 16 and the second portion 18 are sealed to form a first chamber 15 and a second chamber 20, encompassing lumen 21. The first and second chambers can be similar in volume, or one chamber can be larger in volume than the other. For example, in some embodiments according to FIG. 1, the ratio of the volume of the first chamber to the second chamber can be in the range of about 1:1 to about 3:1.

In some embodiments, e.g., as illustrated in FIG. 8, the porous medium 10 can be located in an additional housing, such as vent housing 50. Exemplary housings include those disclosed in International Publication No. WO 91/17809 and U.S. Pat. Nos. 5,126,054 and 5,451,321. These International Publications and Patents also disclose suitable vents 101 (e.g., as illustrated in FIG. 10) such as gas inlets and/or gas outlets.

In some embodiments, the device 100 can also include a cap or closure, e.g., for covering or sealing port 30. For example, in accordance with any embodiments of the device 100 (e.g., with or without a check valve, with or without a liquophilic element), a cap can be used to cover port 30 to prevent the entry of gas, and to uncover port 30 to allow gas to exit the device.

The device 100 may be incorporated into a variety of fluid transfer and/or processing systems or sets. Embodiments of exemplary systems 500, which are preferably parenteral fluid administration sets, are illustrated in FIGS. 6, 7, 9 and 10.

Figure 7:
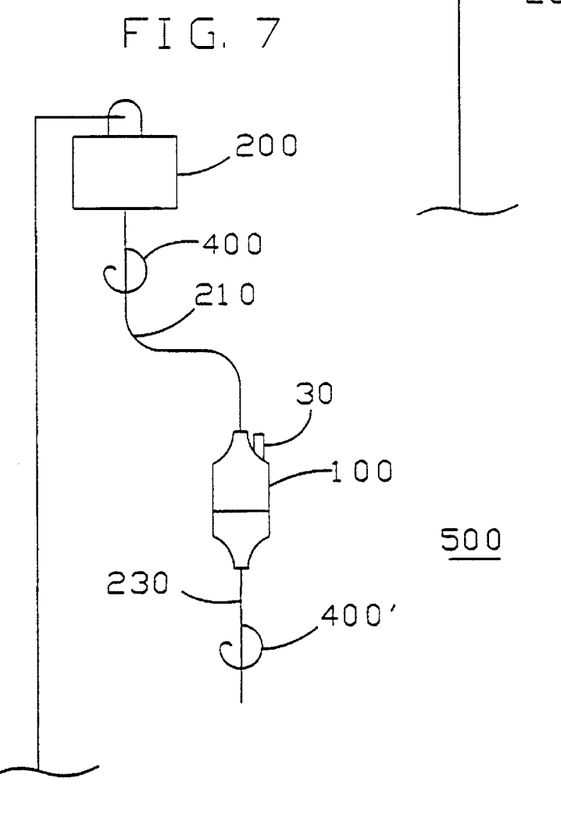
FIG. 7 is an embodiment of another fluid processing system according to the present invention, including a venting device.

Typically, the system includes at least one container for holding the fluid to be transferred, and one or more conduits that provide fluid communication between the container, the device 100, and the destination of the fluid, e.g., a patient receiving the transferred fluid. As illustrated in FIGS. 7, 9, and 10, the system can also include at least one filter for filtering the fluid to be transferred.

The containers 200, 200' which can be used in the system can be constructed of any material compatible with the fluid to be transferred. A wide variety of suitable containers are already known in the art. Typically, container 200, 200' comprises a flexible material, for example, polyvinyl chloride (PVC). An exemplary container is a flexible bag, e.g., as is used for holding blood or blood components. Alternatively, the containers may be composed of a non-flexible material. It is intended that the invention should not be limited by the type or composition of the container being employed.

As with the containers, the conduits 210, 210', 220, and 230 can be constructed of any material that is compatible with the fluid(s) to be transferred. Typically, the conduits comprise flexible material. A preferred material is PVC, for example. As used herein, the conduits are any tubing or means which provide fluid communication between the various components of the administration set. At least one flow control device 400,400' such as a clamp (including, for example, a roller clamp), seal, stopcock, valve, transfer leg closure, or the like, may be associated with at least one of the conduits in order to facilitate a desired function, i.e., to open, close, and/or modulate the desired flow of the fluid (e.g., parenteral fluid) and/or gas. In some embodiments, particularly for some of the embodiments that include administering fluid to a patient, the flow control device 400' downstream of the device 100 comprises a roller clamp to control the flow rate.

Typically, as illustrated in FIGS. 7, 9, and 10, the system also includes at least one filter 300, preferably upstream of device 100, to filter the fluid to be transferred. A variety of filters are suitable for use in the system, e.g., IV filters, e.g., for administering drugs and/or nutrients; and blood filters, including leukocyte filters. Typically, the filter comprises a filter assembly, including a housing having an inlet and an outlet and providing a fluid flow path between the inlet and the outlet, and a porous filter medium for filtering the fluid disposed between the inlet and the outlet and across the fluid flow path.

In some embodiments, the leukocyte filter comprises a synthetic polymeric leukocyte depletion medium, more preferably a synthetic, polymeric, fibrous medium. In an embodiment, the leukocyte depletion medium has a Critical Wetting Surface Tension (CWST) of about 55 dynes/cm or greater, e.g., about 60 dynes/cm or greater. For example, the CWST can be in the range of about 62 dynes/cm to about 100 dynes/cm. Exemplary leukocyte filters include those disclosed in, for example, U.S. Pat. Nos. 4,925,572; 4,880, 548; and 5,217,627.

Embodiments of a method according to the invention include locating the device in a fluid flow path between a source of fluid, e.g., a container, and the intended destination of the fluid, e.g., a patient, and transferring the fluid through the device. For example, referring to the exemplary embodiments illustrated in FIGS. 6, 7, 9, and 10, fluid flow control devices 400,400' such as clamps upstream and downstream of the device 100 are typically closed initially, and then the flow control device upstream of device 100 is opened, to allow fluid to enter the housing. Since the flow control device downstream of the device 100 remains closed, gas (e.g., gas displaced into the housing by liquid passing through the conduit(s)) passes through the vent 3 as the device fills with liquid.

The device 100 can be filled and used (e.g., during fluid administration) without being inverted. Preferably, device 100 remains in an upright, or essentially upright, position during filling and subsequent use. Accordingly, once the operator of the fluid transfer system, e.g., a nurse, opens the appropriate upstream flow control device(s), the device can automatically vent and fill to a desired level, without operator involvement. As a result, there is no need for the operator to carefully monitor the system during priming, and the operator can perform other tasks in the meantime. Since the device automatically fills to a predetermined level, there is no need for the operator to rush back to the system to avoid overfilling. After the device fills to the desired level, the flow control device downstream of device 100 is opened, and the fluid is passed to the desired destination.

Using FIG. 1 (illustrating an embodiment of the device), as well as FIGS. 7, 9, and 10 (illustrating embodiments of the system) for reference, fluid is passed, e.g., by gravity, from container 200 through at least one conduit to device 100, while the flow control device 400' downstream of device 100 is closed. Liquid and gas enter the housing 14 via inlet 1. Preferably, device 100 (FIG. 1) includes a nipple 22 and a port 23, and fluid passes into lumen 21 in the form of droplets. Since the fluid flow path downstream of the device 100 remains closed, the device acts as a reservoir, as second chamber 20 fills with liquid. As the second chamber 20 fills with liquid, gas is displaced. Some of this gas is vented from the device, i.e., the gas passes from the interior of the housing along a gas flow path through porous medium 10 via surface 10b and surface 10a, and through port 4 and gas passageway 5 to the exterior of the housing. In those embodiments wherein the housing includes ribs and channels, e.g., ribs 25 and channels 24 and 27 as illustrated in FIG. 2, gas passes along channels 24 and 27 through port 4 to gas passageway 5 to more efficiently vent the device.

Second chamber 20 (shown in FIG. 1) continues to fill with liquid, and eventually, the level of liquid will reach surface 10b of porous medium 10. Once liquid covers the surface 10b, gas flow through the vent 3 stops, without liquid substantially passing through the medium 10. Once the gas flow stops, the device 100 is filled to the desired level, as gas remaining in the interior of the housing 14 will not be displaceable, and the liquid will stop rising in the housing. Furthermore, in those embodiments wherein porous medium 10 includes a liquophobic element (presenting surface 10a) and a liquophilic element (presenting surface 10b), once liquid covers the liquophilic element, the vent 3 is sealed. Once vent 3 is sealed, gas exterior to the device is prevented from entering the device, even if the liquid level in second chamber 20 decreases. As noted earlier, if desired, the port 30 can be blocked or covered (e.g., with a cap) after the vent 3 is sealed.

In some of those embodiments wherein the porous medium 10 lacks a liquophilic element or layer, the port 30 should be blocked or covered (at least temporarily) after gas flow stops and the liquid covers surface 10b. However, after transfer, e.g., administration, of the fluid is essentially completed, the operator of the system can uncover the port to recover some of the fluid retained in the device 100. For example, after administering the fluid to a patient, the operator can remove the cap, and drain some of the liquid retained in the device and downstream conduit(s) into the patient, and then the operator can manually stop the flow of liquid before gas can reach the patient.

In preferred embodiments, gas flow stops when the device 100 is about ⅔ filled with liquid. Illustratively, when passing a red blood cell-containing fluid such as packed red cells (PRC) or whole blood into the device, the device has a total capacity of, for example, about 15 cc, and gas flow stops when the device contains about 10 cc of liquid. In another embodiment, When passing a platelet-containing fluid such as platelet concentrate (PC) into the device 100, the device has a total capacity of, for example, about 9 cc, and gas flow stops when the device contains about 6 cc of liquid.

Once the device is filled, the liquid can be delivered as desired. For example, using FIGS. 7, 9, and 10 for reference, the flow control device 400' downstream of device 100 (e.g., a flow control device such as a roller clamp) can be opened, and the fluid can be administered to a patient.

In some embodiments, e.g., as illustrated in FIGS. 6, 9, and 10, the system 500 also includes a filter 300 such as a leukocyte depletion filter, and the container 200 (FIG. 6) or 200' (FIGS. 9 and 10) contains a leukocyte-containing biological fluid such as blood or a blood component. Using FIG. 6 for reference (the embodiments of the system illustrated in FIGS. 9 and 10 can be operated similarly), flow control devices 400,400' are typically initially closed, and the flow control device 400 between the container of leukocyte-containing biological fluid and filter 300 is opened. If desired, the container of biological fluid may be squeezed to more efficiently prime the filter 300. Fluid exiting the filter 300 enters the device 100, which vents gas and fills with liquid as described earlier. After the device automatically vents and fills to a desired level, the flow control device 400' downstream of device 100 can be opened, and the liquid can be administered to the patient.

If desired, the device 100 can initially be filled with one fluid, e.g., a non-biological fluid such as saline, and after the device vents gas and fills with this liquid, the liquid is administered and then a second fluid, e.g., a biological fluid that is compatible with the non-biological fluid, is passed through the device and administered.

For example, using the embodiment of the system illustrated in FIG. 10 for reference, wherein the exemplary fluids are saline and biological fluid, container 200 contains saline, and the container 200' contains a leukocyte-containing biological fluid, flow control devices 400,400' are typically initially closed, and then flow control device 400 between the container 200 and the device 100 is opened. Saline enters the device 100 which automatically vents and fills to the desired level.

The flow control device 400 between container 200' and the filter 300 can also be opened, and the filter can be primed as is known in the art. For example, an additional vent 101 such as a gas outlet can be interposed between filter 300 and the junction of conduits 210 and 220; and, with a flow control device 400 (interposed between the gas outlet and the junction of conduits 210 and 220) closed, gas displaced by the biological fluid can be passed through the gas outlet. If the gas outlet includes a liquophilic element and a liquophobic element, gas will pass through the elements until the liquophilic element is covered or wetted with liquid, and gas flow stops. If the gas outlet includes a liquophobic element, the outlet should be capped or blocked after the gas displaced by the biological fluid is passed through the outlet. Alternatively, e.g., in some embodiments wherein the system lacks an additional vent 101 such as a gas outlet, gas displaced by the biological fluid can be passed via conduits 220 and 210 into container 200 after a flow control device 400 interposed, for example, between filter 300 and the junction between conduits 210 and 220, is opened.

If desired, the filter 300 can be primed with one fluid (e.g., biological fluid) and the device 100 can be filled with another fluid (e.g., saline) simultaneously, or nearly simultaneously. For example, using the embodiment of the system illustrated in FIG. 10 for reference, if flow control devices 400 (interposed between the gas outlet and the junction of conduits 210 and 220), and 400' (downstream of the device 100), both remain closed, opening the other flow control devices 400 illustrated in FIG. 10 allows gas to be displaced through vent 101 (downstream of filter 300) and port 30 (of device 100).

In accordance with these embodiments described above, the flow control device 400' downstream of the device 100 is then opened, and the first fluid (e.g., saline) is administered to the patient. Subsequently, the flow control device 400 between container 200 and the device 100 is closed, and the flow control device 400 interposed between the filter 300 and the device 100 is opened. The filtered biological fluid is then administered to the patient.

If desired, the shift from administering one fluid to administering another fluid can be carried out quickly and easily. For example, the filter 300 can be primed with biological fluid, and the device 100 can be filled to the desired level with saline nearly simultaneously as described above. After the device 100 fills to the desired level, flow control device 400' is opened and saline is administered. As soon as it is desirable to administer the filtered biological fluid, the flow control device 400 interposed between container 200 and device 100 is closed, and the flow control device 400 interposed between vent 101 and device 100 is opened. The filtered biological fluid will then pass into device 100 and the fluid is administered to the patient. Administration can be carried out without delaying to prime the filter 300, since the filter 300 was previously primed.

In some embodiments, e.g., wherein the filter 300 comprises a leukocyte depletion filter, the biological fluid is depleted of at least about 99%, more preferably, at least about 99.9%, or more, of the leukocytes as the fluid passes through the leukocyte depletion filter.

As noted above, embodiments of the method can also include capping and uncapping the device 100. For example, the device can include a cap that engages with the housing, e.g., to cover port 30, and the port can be uncapped while the device initially fills with liquid and vents gas. After the device automatically fills to the desired level, the port can be capped at least temporarily as described earlier. If desired, the port can remain capped while the fluid(s) are subsequently administered to the patient, e.g., to provide an extra barrier preventing gas from the outside environment from entering the device 100 through the port 30.

In a variation of the embodiments illustrated in FIGS. 1 and 9, porous medium 10 comprises a liquophobic element having surface 10a and surface 10b, and porous medium 10 lacks a liquophilic element. Since surfaces 10a and 10b are both liquophobic, both surfaces can resist the passage of liquid(s) therethrough. Typically, as described above, the port 30 should be closed, covered or blocked after liquid covers surface 10b of porous medium 10. Additionally, or alternatively, a liquid can be placed in gas passageway 5 to provide a column of liquid in the passageway. Since this liquid in the passageway 5 is typically discarded along with the device after the device is used, it is more economical to utilize a drug and nutrient free liquid such as water in the passageway, in contrast with the parenteral fluid to be passed through the device and into the patient.

In accordance with another embodiment, the device 100 can include a flow control device such as a valve that allows gas to pass from the device and prevents gas from entering the device. For example, the flow control device can be disposed in the gas passageway 5, or a cap can include the flow control device 401. Illustratively, in an embodiment of the invention wherein device 100 has a liquophobic porous medium 10, and includes a check valve in the gas passageway 5, gas passes through the porous medium 10, through the check valve in the gas passageway 5, and through the port 30. The check valve allows gas to exit the device through port 30, and prevents gas from entering the device through the port 30.

Using FIGS. 1 and 7 for reference, as parenteral fluid passes from container 200 into the device 100, liquid and gas enter the housing via inlet 1. As the device fills with liquid, gas is displaced, and passes through surfaces 10b and 10a, through the column of liquid in passageway 5, and through port 30. Once the level of fluid in second chamber 20 reaches surface 10b, gas flow through medium 10 stops, without liquid passing through the medium 10. Moreover, the liquid in passageway 5 prevents gas or air exterior to the device from entering the device, even if the liquid level in second chamber 20 decreases. However, after the fluid level reaches surface 10b, additional gas entering the housing via inlet 1 can be vented through surfaces 10a and 10b, through the column of liquid in passageway 5, and through port 30.

Alternatively, using FIGS. 1 and 9 for reference, as parenteral fluid passes from container 200 into the device 100, liquid and gas enter the housing via inlet 1. As the device fills with liquid, gas is displaced, and passes through surfaces 10b and 10a, through the flow control device 401 (e.g., a check valve) in passageway 5, and through port 30. Once the level of fluid in second chamber 20 reaches surface 10b, gas flow through medium 10 stops, without liquid passing through the medium 10. Moreover, the flow control device 401 in passageway 5 prevents gas or air exterior to the device from entering the device, even if the liquid level in second chamber 20 decreases. However, after the fluid level reaches surface 10b, additional gas entering the housing via inlet 1 can be vented through surfaces 10a and 10b, through the flow control device in passageway 5, and through port 30. If desired, the device can also include a cap that engages with the housing, e.g., to cover port 30. In those embodiments, the device is uncapped while gas is vented, and capped while parenteral fluid is being administered.

Of course, in some alternative embodiments, e.g., wherein the cap (rather than the gas passageway 5) includes the flow control device 401 such as a check valve, the device can remain capped while venting.

In some of those embodiments wherein a plurality of parenteral fluids are utilized, e.g., in accordance with the embodiments as illustrated in FIGS. 9 and 10, wherein the porous medium 10 comprises a liquophobic medium, and lacks a liquophilic element or portion, the first parenteral fluid (e.g., saline or a blood component) may be passed into the device and gas is vented as described above. After gas is vented, the parenteral fluid is administered. Typically (using the embodiment illustrated in FIG. 9 for reference), when it is desirable to utilize a second (e.g., a different) parenteral fluid, the flow control devices 400,400' downstream of the device 100, and interposed between the device 100 and the container for the first parenteral fluid, are closed, and the flow control device 400 interposed between the container for the second parenteral fluid and the device 100 is opened. The second parenteral fluid is passed into the device 100. Gas displaced by the second parenteral fluid into the device can be vented through the liquophobic porous medium 10 until the medium is contacted with the second parenteral fluid. The downstream flow control device 400' (e.g., associated with conduit 230) can then be opened, and the second parenteral fluid can be administered. The flow control device 401 and/or the capping of the port 30 will prevent gas from entering the device through port 30.

All of the references cited herein, including publications, patents, and patent applications, are hereby incorporated in their entireties by reference.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. A device for transferring fluid comprising:
a housing comprising a fluid reservoir for gas and liquid and providing a gas flow path, wherein the housing includes a plurality of concentric channels along the gas flow path; and
a vent communicating with the housing;
said vent comprising a porous medium that allows gas in the housing to pass through the medium until the medium is contacted by a liquid;
said vent and said housing being cooperatively arranged to allow the gas to be passed through the plurality of concentric channels along the gas flow path and vented from the housing and for liquid to fill the housing to a predetermined level that is less than the total liquid capacity of the housing.

2. The device of claim 1, wherein the housing provides a gas flow path and the housing includes a plurality of concentric channels along the gas flow path, wherein the drip chamber is arranged to allow gas to pass through the porous medium, along the plurality of concentric channels, and from the housing.

3. The device of claim 2, wherein the housing contains the vent.

4. The device of claim 2, wherein the vent and the housing are cooperatively arranged to pass gas from the housing and then through the porous medium.

5. The device of claim 2, including a fluid passageway extending into the interior of the housing, said passageway communicating between the interior of the housing and the porous medium.

6. The device of claim 2, wherein the porous medium has a bacterial blocking pore structure.

7. A The device of claim 1 wherein the vent comprises a liquid sealable porous medium.

8. The device of claim 1, wherein the housing includes a plurality of radial channels along the gas flow path, said vent and said housing being cooperatively arranged to allow the gas to be passed through the plurality of concentric channels and the plurality of radial channels along the gas flow path.

9. A system for transferring fluid comprising:
a device for transferring fluid comprising a housing comprising a fluid reservoir for gas and liquid and providing a gas flow path, wherein the housing includes a plurality of concentric channels along the gas flow path; and
a vent communicating with the housing;
said vent comprising a porous medium that allows gas in the housing to pass through the medium until the medium is contacted by a liquid; said vent and said housing being cooperatively arranged to allow the gas to be passed through the plurality of concentric channels along the gas flow path and vented from the housing and for liquid to fill the housing to a predetermined level that is less than the total liquid capacity of the housing; and a filter including a porous medium for filtering the fluid to be transferred, wherein the filter is in fluid communication with the device.

10. The system of claim 9, wherein the device is arranged to allow gas to pass through the vent comprising the porous medium, along the plurality of concentric channels, and from the housing.

11. A method for transferring fluid comprising:

passing a fluid into a device comprising a housing including a fluid reservoir for gas and liquid and providing a gas flow path, wherein the housing includes a plurality of concentric channels along the gas flow path; and a vent communicating with the housing, said vent comprising a porous medium that allows gas in the housing to pass through the medium until the medium is contacted by a liquid;

passing liquid into the housing and passing gas through the porous medium and through the plurality of concentric channels along the gas flow path until the liquid contacts the porous medium and the housing is filled to a predetermined level that is less than the total liquid capacity of the housing.

12. The method of claim 11, wherein the device comprises a drip chamber.

13. The method of claim 11, including filtering the fluid before passing it into the device.

14. The method of claim 11, wherein the device is not inverted while passing the fluid into the device.

15. The method of claim 11, wherein the device housing is not compressed before passing the fluid into the device.

16. The method of claim 11, comprising passing a biological fluid through the device.

17. The method of claim 11, comprising passing two or more fluids through the device.

18. The method of claim 17, therein at least one fluid is a biological fluid, and the method includes removing leukocytes from the fluid to provide a leukocyte-depleted biological fluid, and passing the leukocyte-depleted biological fluid through the device.

19. The method of claim 11, wherein passing the fluid into the device comprises passing liquid and gas displaced by the liquid into the housing.

20. The method of claim 11, including passing fluid through the device, and administering the fluid to a patient.

21. The method of claim 11, wherein passing the fluid into the device includes passing the fluid into a device comprising a housing and a vent communicating with the housing, the vent comprising a liquid sealable porous medium.

22. A device for transferring fluid comprising:

a housing comprising a fluid reservoir for gas and liquid and providing a gas flow path, wherein the housing includes a plurality of radial channels along the gas flow path; and a vent communicating with the housing; said vent comprising a porous medium that allows gas in the housing to pass through the porous medium until the porous medium is contacted by a liquid;

said vent and said housing being cooperatively arranged to allow the gas to be passed through the plurality of radial channels along the gas flow path and vented from the housing and for liquid to fill the housing to a level that is less than the total liquid capacity of the housing.

23. The device of claim 22, wherein the porous medium has a bacterial blocking pore structure.

24. A device for transferring fluid comprising:

a housing comprising a fluid reservoir for gas and liquid and providing a gas flow path, wherein the housing includes at least one annular channel along the gas flow path; and a vent communicating with the housing;
said vent comprising a porous medium that allows gas in the housing to pass through the porous medium until the porous medium is contacted by a liquid, the porous medium comprising a liquophobic element and a liquophilic element;

said vent and said housing being cooperatively arranged to allow the gas to be passed through the porous medium and through the at least one annular channel along the gas flow path and vented from the housing and for liquid to fill the housing to a level that is less than the total liquid capacity of the housing.

25. The device of claim 24, wherein the housing includes a plurality of radial channels along the gas flow path, said vent and said housing being cooperatively arranged to allow the gas to be passed through the at least one annular channel and the plurality of radial channels along the gas flow path.

26. The device of claim 24, wherein the porous medium has a bacterial blocking pore structure.

27. A system for transferring fluid comprising:

a device for transferring fluid comprising a housing suitable for holding gas and a liquid; and a vent comprising a porous medium that allows gas but not liquid in the housing to pass through the porous medium until the porous medium is contacted by the liquid and gas flow stops, the porous medium including a liquophilic element and a liquophobic element, the device allowing a desired amount of liquid to held in the housing wherein the amount is less than the total liquid capacity of the housing; and a filter including a porous medium for filtering the fluid to be transferred the porous medium allowing liquid to pass therethrough, wherein the filter is in fluid communication with the device.

28. A device for transferring fluid comprising:

a housing comprising a fluid reservoir for gas and liquid and providing a gas flow path; and a vent communicating with the housing, said vent comprising a porous medium including a liquophobic element superimposed on a liquophilic element, said porous medium allowing gas in the housing to pass through the liquophilic element and the liquophobic element until the liquophilic element is contacted by the liquid and gas flow stops, said vent and said housing being cooperatively arranged to allow the gas to be passed along the gas flow path and vented from the housing and for liquid to fill the housing to a predetermined level that is less than the total liquid capacity of the housing.

29. The device of claim 28, wherein the porous medium has a bacterial blocking pore structure.

* * * * *